United States Patent [19]

Schramm et al.

[11] Patent Number: 6,056,941

[45] Date of Patent: May 2, 2000

[54] KIT FOR THE PREPARATION OF TECHNETIUM TC 99M TEBOROXIME MYOCARDIAL PERFUSION AGENT

[75] Inventors: Ernest Schramm, North Brunswick; Margaret Newborn, Hamilton; Julius P. Zodda; Thomas Katona, both of Mercerville; Jo Anna Monteferrante, Flemington, all of N.J.

[73] Assignee: Bracco Research USA, Princeton, N.J.

[21] Appl. No.: 09/363,132

[22] Filed: Jul. 28, 1999

[51] Int. Cl.[7] ............................ A61K 51/00; A61M 36/14
[52] U.S. Cl. .................... 424/1.73; 424/1.11; 424/1.65; 534/10; 534/14
[58] Field of Search .................. 424/1.11, 1.65, 424/1.21, 1.69, 9.1, 9.2; 206/223, 569, 570; 534/7, 10–16

[56] References Cited

U.S. PATENT DOCUMENTS

| | | | |
|---|---|---|---|
| 4,705,849 | 11/1987 | Nunn et al. | 534/14 |
| 4,714,605 | 12/1987 | Feld | 524/1.1 |
| 4,727,064 | 2/1988 | Pitha | 514/58 |
| 4,871,836 | 10/1989 | Francesconi et al. | 534/10 |
| 5,069,900 | 12/1991 | Linder | 424/1.11 |
| 5,070,081 | 12/1991 | Majid et al. | 514/58 |
| 5,112,595 | 5/1992 | Woulfe et al. | 424/1.1 |
| 5,118,797 | 6/1992 | Jurisson et al. | 534/10 |
| 5,183,653 | 2/1993 | Linder et al. | 424/1.11 |
| 5,300,280 | 4/1994 | De Rosch et al. | 424/1.53 |

OTHER PUBLICATIONS

Szente et al., Spontaneous Opalescence of Aqueous γ–Cyclodextrin Solutions: Complex Formations or Self–Aggregation?, J.of Pharm. Sciences, vol. 87, No. 6, Jun. 1998, pp. 778–781.

McCoy, M, Cyclodextrins: Great Product Seeks A Market, C& EN, Mar. 1, 1999, pp. 25–27.

*Primary Examiner*—José G. Dees
*Assistant Examiner*—Dameron Jones
*Attorney, Agent, or Firm*—Imre Balogh

[57] ABSTRACT

A kit containing a solution of boronic acid adducts of technetium-99 m dioxime complexes; and hydroxypropyl gamma cyclodextrin to maintain the solution free of particulate matter originating from the formulation.

5 Claims, No Drawings

KIT FOR THE PREPARATION OF TECHNETIUM TC 99M TEBOROXIME MYOCARDIAL PERFUSION AGENT

BACKGROUND OF THE INVENTION

1. Field of the Invention

The present invention relates to imaging agents. More particularly, the invention relates to imaging agents for imaging the myocardium in patients with suspected coronary artery diseases using rest and stress techniques.

2. Reported Developments

U.S. Pat. No. 4,705,849 discloses boronic acid adducts of technetium-99 m dioxime complexes for imaging the myocardium, hepatobiliary system, brain and blood pool in humans and other mammalian species. One of these complexes is used in a kit for imaging the myocardium, and sold under the trademark CARDIOTEC®.

The kit comprises a 5 ml reaction vial which contains a sterile, nonpyrogenic, lyophilized formulation of: 2.0 mg cyclohexanedione dioxime;

2.0 mg methyl boronic acid;

2.0 mg pentetic acid;

9.0 mg citric acid;

100.0 mg sodium chloride;

50.0 mg gamma cyclodextrin; and 0.058 mg (maximum) total tin expressed as stannous chloride ($SnCl_2$), 0.020 mg (minimum) stannous chloride ($SnCl_2$).

To the 5 ml reaction vial, containing the lyophilized formulation, 1 ml sodium pertechnetate Tc-99 m injection is added containing 370 to 3,700 MBq (10–100 mCi) to obtain a solution which is then heated at 100° C. for 15 minutes to obtain the diagnostic agent Technetium Tc-99 m Teboroxime.

The diagnostic agent has been used by health care professionals over several years and it has been found useful in distinguishing normal from abnormal myocardium in patients with suspected coronary artery diseases using rest and stress techniques.

The CARDIOTEC® kit contains a package insert instructing the diagnosticians to visually inspect the reconstituted formulation subsequent to the addition of the pertechnetate Tc-99 m into the reaction vial and the heating step. The formulation is to be used only if the solution is clear to slightly opalescent and free of particulate matter and discoloration.

The occurrence of particulate matter formation and discoloration of the diagnostic agent necessitated an investigation for finding a cause thereof. During the course of the investigation the solution was filtered to remove the particulate matter, which appeared to be successful. However, upon further investigation it was found that the problem of particulate matter formation and discoloration cannot be eliminated by filtration. Although immediately after filtration the solution is clear, the turbidity and discoloration reappear after a period of time necessitating re-filtration or discarding of the solution.

Thus, the additional step of filtration in producing the diagnostic agent was impractical, as it was cumbersome and inconvenient to the diagnosticians mainly for the reasons that: diagnostic facilities are not ordinarily equipped with such filtration devices having adequate radioactive shielding and the necessity to perform the filtration procedure immediately before use as it was not effective over the shelf-life of the reconstituted product.

Applicants in conducting extensive studies with the boronic acid adducts of technetium-99 m dioxime complexes disclosed in U.S. Pat. No. 4,705,849, which patent is incorporated herein by reference in its entirety, found a solution to the problems of particulate matter formation and discoloration.

Accordingly, the object of the present invention is to provide improved solutions of boronic acid adducts of technetium-99 m dioxime complexes for mycocardial infusion, in which no particulate matter is formed or discoloration occurs upon the injection of pertechnetate Tc-99 m into the reaction vial containing the lyophilized ingredients or during the shelf-life of the so-produced diagnostic agent formulation.

SUMMARY OF THE INVENTION

We have surprisingly discovered that the addition of hydroxypropyl gamma cyclodextrins, preferably 2-hydroxypropyl gamma cyclodextrin which replaces the gamma cyclodextrin used in the CARIDIOTEC® formulation of the lyophilized ingredients in the reaction vial, provides clear solutions when the lyophilized ingredients are reconstituted by the addition of pertechnetate Tc-99 m. Accordingly, the present invention comprises a kit having (a) first container such as a vial which contains lyophilized ingredients and (b) second container such as a vial or syringe which contains sodium pertechnetate Tc-99 m.

(a) First container, such as a vial preferably contains:

1 to 3 mg cyclohexanedione dioxime;

1 to 3 mg methyl boronic acid;

1 to 3 mg pentetic acid;

8 to 10 mg citric acid;

5 to 10 mg sodium chloride;

30 to 50 mg hydroxypropyl gamma cyclodextrin; and 0.030 to 0.060 mg stannous chloride ($SnCl_2$).

(b) Second container, such as a vial contains:

1 to 3 ml pertechnetate Tc-99 m having 370 to 3,700 MBq (10–100 mCi) in physiological saline or derived from generator sources.

In preparing Technetium Tc-99 m Teboroxime the sodium pertechnetate Tc-99 m is added from the second container to the first container which contains the lyophilized ingredients to provide a sterile mixture, swirling the contents of the first container and heating the same at about 100° C. for 5 to 15 minutes to obtain a solution, and cooling the solution which is then ready for parenteral administration to a patient.

The diagnostic formulation obtained has been tested and found to be free of particulate matter and discoloration for at least six hours without filtration or other means to eliminate the presence of particulate matter or the appearance of discoloration.

In another aspect the present invention is directed to a method for providing a radiopharmaceutical kit, the method comprising:

(1) providing a first container, such as a vial containing a solution of 1 to 3 mg cyclohexanedione dioxime;

1 to 3 mg methyl boronic acid;

1 to 3 mg pentetic acid;

8 to 10 mg citric acid;

5 to 10 mg sodium chloride;

30 to 50 mg hydroxypropyl gamma cyclodextrin; and 0.030 to 0.060 mg stannous chloride ($SnCl_2$).

(2) lyophilizing the content of the first container;

(3) providing a second container containing;
   1 to 5 ml pertechnetate Tc-99 m having 370 to 3,700 MBq (10–100 mCi) in physiological saline or from generator sources;
(4) injecting the content of the second container into the first container to obtain a mixture thereof;
(5) heating the solution at about 100° C. to obtain a solution thereof; and
(6) cooling the solution to room temperature for administration to a patient.

DETAILED DESCRIPTION OF THE INVENTION

The formulation of the present invention for myocardial diagnosis utilizes boric acid adducts of technetium-99 m dioxime complexes of formula I:

$$^{99m}TcX(Y)_3Z \quad I$$

wherein X is an anion;
Y is vicinal dioxime of formula II;

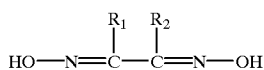

or a pharmaceutically acceptable salt thereof;
   $R_1$ and $R_2$ are independently, hydrogen, halogen, alkyl, aryl, amino or a 5 or 6-membered nitrogen or oxygen containing heterocycle, or together
   $R_1$ and $R_2$ are-$(CR_8R_9)n$
wherein n is 3 to 6 and
   $R_8$ and $R_9$ are independently hydrogen or alkyl; and
   Z is a boron derivative of formula III:
      B—$R_3$ III
wherein
   $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $(R_4R_5N)$-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

The definition of radicals and moieties are as follows.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups. Additional exemplary aryl groups for the instance wherein $R_3$ is aryl include 3-(5-dimethylamino-1-naphthalensulfonyl-amino)phenyl, 3-[4-[3'-phenyl-2'pyrazolin-1,1'-yl]benzene-sulfonyl-amino] phenyl, 3-(pyrenesulfamido)-phenyl, 3-[4-(4-dimethylamino- 1-naphthylazo)-3 -(methoxyphenyl-sulfamido)] phenyl, 3-[4-(4-dimethylamino-1-phenylazo) phenylthioureido] phenyl.

Preferred "cycloalkyl" and "cycloalkenyl" groups are those having 5, 6 or 7 carbon atoms. The terms include those groups substituted with alkyl, alkoxyl, aryl, carboxyalkyl, arylalkyl or $(R_4R_5N)$-alkyl groups.

The terms "halide", "halo" and "halogen" refer to fluorine, chlorine, bromine and iodine.

The expression "5 or 6-membered nitrogen containing heterocycle" refers to all 5 and 6-membered rings containing at least one nitrogen atom. Exemplary aliphatic groups are dihydro derivatives of a compound having the formula

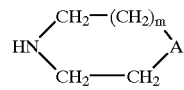

wherein m is 0 or 1 and A is O, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expressions "5 or 6 membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via hetero atom or carbon atom.

The expression "5 or 6-membered nitrogen or oxygen containing heterocycle" refers to all 5 and 6-membered rings containing at least one nitrogen or oxygen atom. Exemplary groups are those described above under the definition of the expression "5 or 6-membered nitrogen containing heterocycle". Additional exemplary groups are 1,4-dioxanyl and furanyl.

Preparation of the complexes

The complexes are preferably prepared by using technetium-99 m in the form of the pertechnetate ion which is commercially available. Alternatively, the pertechnetate ion can be prepared as described in U.S. Pat. Nos. 3,369,121 and 3,920,995. The generators are eluted with a saline solution to obtain the sodium salt of the pertechnetate ion.

The salt of pertechnetate ion is combined with a source of anion, a boronic acid derivative of the formula

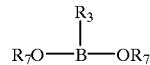

or a pharmaceutically acceptable salt thereof,
wherein
$R_7$ is hydrogen, alkyl or aryl, and
dioxime having the formula

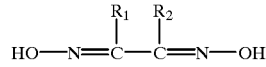

or a pharmaceutically acceptable salt thereof.

The source of an anion is preferably sodium chloride in a concentration of from about 0.1 to about 0.5 molar.

The boronic acid derivative should be present in a concentration range of from about 5 to about 200 millimolar; while the dioxime should be present in the concentration range of from about 9 to about 43 millimolar.

The reaction mixture should also contain a reducing agent. Stannous ion is the preferred reducing agent, and can be introduced in the form of a stannous salt such as a stannous halide (e.g., stannous chloride or stannous fluoride). The reducing agent should be present in a concentration of about 1.5 micromolar to 6.6 millimolar.

Complexing or chelating agents as well as accelerators or catalysts known in the art may also be used in preparing the diagnostic agent of the present invention.

Illustrative examples of the complexes include:

$^{99m}$Tc (chlorine) (dimethyl glyoxime)$_3$ methoxy boron;
$^{99m}$Tc (chlorine) (dimethyl glyoxime)$_3$ ethoxy boron;
$^{99m}$Tc (chlorine) (dimethyl glyoxime)$_3$ hydroxy boron;
$^{99m}$Tc (chlorine) (dimethyl glyoxime)$_3$ propyloxy boron;
$^{99m}$Tc (chlorine) (dimethyl glyoxime)$_3$ hexyloxy boron;
$^{99m}$Tc (chlorine) (dimethyl glyoxime)$_3$ 1-methylpropyl boron;
$^{99m}$Tc (bromine) (dimethyl glyoxime)$_3$ butyl boron;
$^{99m}$Tc (iodine) (dimethyl glyoxime)$_3$ butyl boron;
$^{99m}$Tc (fluorine) (dimethyl glyoxime)$_3$ butyl boron;
$^{99m}$Tc (chlorine) (dimethyl glyoxime)$_3$ 3-(4-morpholinyl) propyl boron;
$^{99m}$Tc (chlorine) (dimethyl glyoxime)$_3$ 2-phenylethyl boron;
$^{99m}$Tc (chlorine) (1,2-cyclohexanedione dioxime)$_3$ methyl boron; and
$^{99m}$Tc (chlorine) (dimethyl glyoxime)$_3$ 4-formylphenyl boron.

Illustrative of the preparation of the diagnostic agent is shown in Examples 1 and 2.

EXAMPLE 1

$^{99m}$Tc (chlorine)(1,2-cyclohexanedionedioxime)$_3$, 3-(1-piperidinyl)propyl boron.

Into a 5 ml siliconized vial were measured 0.5 mg of 1,2-cyclohexanedione dioxime in 0.1 ml of ethanol, 1.0 mg of 3-(1-piperidinyl)propane boronic acid monohydrochloride, 0.2 ml of saturated sodium chloride, 10 mg of citric acid, 40 mg of hydroxypropyl gamma cyclodextrin and 50 μl of saturated stannous pyrophosphate.

Sodium pertechnetate Tc-99 m in physiological saline (0.2 ml) was added to this vial which was then heated at 100° C. for 5 minutes yielding 84% of the title complex.

The solution remained clear without containing particulate matter for more than 6 hours after preparation.

EXAMPLE 2

$^{99m}$Tc (chlorine)(1,2-cyclohexanedione dioxime)$_3$ methyl boron.

Into a 5 ml serum vial were measured 2.0 mg of 1,2-cyclohexanedione dioxime, 2.0 mg of methane boronic acid, 10 mg of citric acid, 10 mg of sodium chloride, 1.0 mg of diethylenetriamine pentaacetic acid, 45 mg of hydroxypropyl gamma cyclodextrin, 50 micrograms of SnCl$_2$ and 0.5–3 μl of concentrated hydrochloric acid.

Sodium pertechnetate Tc-99 m in physiological saline (0.5 ml) was added to the vial which was then heated at 100° C. for 5 minutes yielding 85% of the title complex.

The solution remained clear without containing particulate matter for more than 6 hours after preparation.

Testing of the diagnostic agent

Technetium Tc-99 m decays by isometric transition with a physical half-life of 6.02 hours. The fractions that remain at selected intervals after the initial calibration are shown in Table I.

TABLE I

Physical Decay Chart: Tc-99m half-life 6.02 hours

| Hours | Fraction Remaining | Hours | Fraction Remaining |
|---|---|---|---|
| 0* | 1.000 | 7 | 0.447 |
| 1 | 0.891 | 8 | 0.398 |
| 2 | 0.794 | 9 | 0.355 |
| 3 | 0.708 | 10 | 0.316 |
| 4 | 0.631 | 11 | 0.282 |
| 5 | 0.562 | 12 | 0.251 |
| 6 | 0.501 | | |

*Calibration time

Following intravenous administration in normal subjects, Technetium Tc-99 m Teboroxime was rapidly cleared from the circulation. Table II approximates the effective clearance of Technetium Tc-99 m Teboroxime from the heart and liver.

TABLE II

| Time | Heart* | Liver |
|---|---|---|
| 5 min | 2.3% | 23% |
| 10 min | 1.7% | 33% |
| 15 min | 1.5% | 32% |
| 20 min | 1.3% | 27% |
| 1 hr | 1.1% | 24% |
| 2 hr | 0.8% | 18% |
| 4 hr | 0.6% | 17% |

*Peak heart uptake occurs within 2 min.

The estimated absorbed radiation doses to organs and tissues of an average subject (70 kg) from intravenous injection totaling 1850 MBq (50 millicuries) of Technetium Tc-99 m Teboroxime are shown in Table III.

TABLE III

Estimated Absorbed Radiation Doses Absorbed Radiation Dose

| Tissue | mGy/1650 MBq | Rads/50 mCi |
|---|---|---|
| Brain | 6.30 | 0.63 |
| Gallbladder Wall | 48.85 | 4.89 |
| Small Intestine | 33.85 | 3.39 |
| Upper Large Intestine | 61.50 | 6.15 |
| Lower Large Intestine | 43.60 | 4.36 |
| Heart Wall | 10.10 | 1.01 |
| Kidneys | 10.10 | 1.01 |
| Liver | 31.00 | 3.10 |
| Lungs | 14.00 | 1.40 |
| Spleen | 7.45 | 0.75 |
| Thyroid | 5.35 | 0.54 |
| Ovaries | 18.05 | 1.81 |
| Testes | 5.20 | 0.52 |
| Red Marrow | 8.30 | 0.83 |
| Urinary Bladder Wall | 13.70 | 1.37 |
| Total Body | 8.30 | 0.83 |

Post-reconstitution appearance of CARDIOTEC® containing gamma cyclodextrin.

An investigation was conducted to determine the size, identity and cause of particles in reconstituted CARDIOTEC® containing gamma cyclodextrin. The investigation revealed that shortly after reconstitution a fine haze of suspended particles appeared which were identified as gamma cylcodextrin using FT-IR. Stereomicroscopic examination revealed that a colorless residue, identified as gamma cyclodextrin, consisted of small clusters of particles, ranging in size from 10 to 40 μm. Individual particles ranged from 0 to 10am, with a few as large as 20 μm.

Visual appearance of CARDIOTEC® formulated with gamma cyclodextrin vs. hydroxypropyl gamma cyclodextrin.

Four batches of CARDIOTEC® solutions were prepared: batches 100 and 200 were formulated with gamma cyclodextrin; and batches 300 and 400 were formulated with hydroxypropyl gamma cyclodextrin. The solutions were visually observed with the following results shown in Table IV.

TABLE IV

Post-reconstitution appearance of CARDIOTEC ® containing gamma cyclodextrin vs. hydroxypropyl gamma cyclodextrin (comparative test).

| Gamma Cyclodextrin | | Hydroxy Propyl Gamma Cyclodextrin | |
|---|---|---|---|
| Batch No. | Visual Appearance | Batch No. | Visual Appearance |
| 100 | Opalescent/Suspended Particles | 300 | Clear Particle Free |
| 200 | Clear/Slightly Opalescent Few Undissolved Particles | 400 | Clear Particle Free |

The visual appearance test of reconstituted CARDIOTEC® is user subjective with no numerical reference point. The present test under this heading describes a semi-quantitative alternate method for the determination of the appearance of reconstituted vials of CARDIOTEC® based on the British Pharmacopoeia clarity of solution test. (British Pharmacopoeia 1993, Volume II, Appendix IV B, pp. A107–108.)

Experimental

The British Pharmacopoeia method for clarity measures the degree of opalescence and expresses it in terms of four reference suspensions (I–IV). Reference suspension I is the least opalescent and reference suspension IV is the most opalescent. A pooled sample of CARDIOTEC® is assigned a number by comparing the appearance of the sample to the appearance of the reference suspensions. Samples are reported as less than (<) the reference suspension number which is more opalescent than the sample. A liquid is considered clear if its clarity is the same as that of water, or if its opalescence is not more pronounced than that of reference suspension I.

The British Pharmacopoeia test (≈15 mL total volume) is performed using 16 pooled vials of CARDIOTEC® reconstituted with 1 mL of saline. A British Pharmacopoeia value of less than or equal to I (≦) would indicate a clear solution while a larger reported British Pharmacopoeia value would indicate a greater degree of opalescence.

The result of comparative testing is shown in Table V.

Table V

Appearance Results on Batches of CARDIOTEC® Formulated with Gamma Cyclodextrin vs. Hydroxy Propyl-Gamma Cyclodextrin for up to Six Hours after Reconstitution, when Tested According to the British Pharmacopoeia Clarity Test.

| Gamma Cyclodextrin | | Hydroxy Propyl-Gamma Cyclodextrin | |
|---|---|---|---|
| Batch No. | Visual Appearance | Batch No. | Visual Appearance* |
| 100 | >III | 300 | <I, clear |
| 200 | >III | 400 | ≦I, clear |
| — | — | 500 | ≦I, clear |

*Method: BP Clarity Test (16 vials, 1.0 mL reconstitution volume)

Having described the invention, it will be apparent to those skilled in the art that various modification may be made without departing from the spirit thereof Accordingly, it is intended that the scope of the present invention be limited solely by the scope of the claims that follow.

What is claimed is:

1. In an improved kit for myocardial diagnosis of a patient with suspected coronary artery diseases using rest and stress techniques, said kit having
   (a) a first container containing lyophilized ingredients; and
   (b) a second container containing technetium TC-99 m; wherein
   said first container contains
   5 to 15 mg sodium chloride, or sodium bromide;
   1 to 3 mg of boronic acid derivative, or compounds which can react in situ to form a boronic acid derivative, having the formula

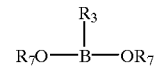

or a pharmaceutically acceptable salt thereof, wherein $R_3$ is hydroxy, alkyl, alkenyl, cycloalkyl, cycloalkenyl, aloxy, carboxyalkyl, carboxyalkenyl, hydroxyalkyl, hydroxalkenyl, alkoxyalkyl, aloxy-alkenyl, haloalkyl, haloalkenyl, aryl, arylalkyl, or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and $R_7$ is hydrogen, alkyl or aryl;
   1 to 3 mg of a dioxime having the formula

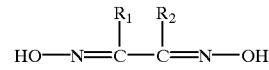

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_2$ and $R_3$ are —$(CH_2R_9)$— wherein n is 3, 4, 5, or 6 and $R_8$ and $R_9$ are each independently hydrogen or alkyl;
   0.03 to 0.06 mg stannous chloride;
   1 to 3 mg pentetic acid; and
   8 to 10 mg citric acid;
   and said second container contains
   1 to 3 ml of technetium Tc-99 m in physiological saline containing 10 to 100 mCi;
   wherein the improvement comprises:
      30 to 50 mg hydroxypropyl gamma cyclodextrin added to said first container.

2. The kit for myocardial diagnosis of a patient according to claim 1, wherein said dioxime is selected from the group consisting of:

dimethyl glyoxime, 1,2-cyclohexanedione dioxime, 1,2-ethanedione dioxime,

α-furyldioxime, 1, 2-cyclopentanedione dioxime and 3-methyl-1, 2-cyclopentanedione dioxime.

3. The kit for myocardial diagnosis of a patient according to claim 1, wherein said boronic acid derivative is selected from the group consisting of:

B-alkyl,

B-alkoxy,

B-benzyl and

B-cycloalkyl.

4. The kit for myocardial diagnosis of a patient according to claim 1 wherein when said technetium Tc-99 m is added to the first container forms a complex with the content thereof, said complex selected from the group consisting of:

$^{99m}$Tc (chlorine) (dimethyl glyoxime)$_3$ methoxy boron;

$^{99m}$Tc (chlorine) (dimethyl glyoxime)$_3$ hydroxy boron;

$^{99m}$Tc (chlorine) (dimethyl glyoxime)$_3$ ethoxy boron;

$^{99m}$Tc (chlorine) (dimethyl glyoxime)$_3$ propyloxy boron;

$^{99m}$Tc (chlorine) (dimethyl glyoxime)$_3$ hexyloxy boron;

$^{99m}$Tc (chlorine) (dimethyl glyoxime)$_3$ 1-methylpropyl boron;

$^{99m}$Tc (bromine) (dimethyl glyoxime)$_3$ butyl boron;

$^{99m}$Tc (iodine) (dimethyl glyoxime)$_3$ butyl boron;

$^{99m}$Tc (fluorine) (dimethyl glyoxime)$_3$ butyl boron;

$^{99m}$Tc (chlorine) (dimethyl glyoxime)$_3$ 3-(4-morpholinyl) propyl boron;

$^{99m}$Tc (chlorine) (dimethyl glyoxime)$_3$ 2-phenylethyl boron;

$^{99m}$Tc (chlorine) (1,2-cyclohexanedione dioxime)$_3$ methyl boron; and $^{99m}$Tc (chlorine) (dimethyl glyoxime)$_3$ 4-formylphenyl boron.

5. In an improved kit for myocardial diagnosis of a patient with suspected coronary artery diseases using rest and stress techniques said kit; having a) a first container containing lyophilized ingredients containing 1 to 3 mg cyclohexanedione dioxime;

1 to 3 mg methyl boronic acid;

8 to 10 mg citric acid;

5 to 10 mg sodium chloride;

and 0.030 to 0.060 mg stannous chloride ($SnCl_2$); and b) a second container containing 1 to 3 ml technetium Tc-99 m in physiological saline;

wherein the improvement comprises:

30 to 50 mg hydroxypropyl gamma cyclodextrin added to said first container.

* * * * *